US009446401B2

(12) United States Patent
Nodin

(10) Patent No.: US 9,446,401 B2
(45) Date of Patent: *Sep. 20, 2016

(54) CONTAINER FOR THE ASEPTIC TRANSFER OF A BIOPHARMACEUTICAL PRODUCT

(75) Inventor: Gaelle Nodin, Saint Maximin la Sainte Baume (FR)

(73) Assignee: SARTORIUS STEDIM FMT SAS, Aubagne (FR)

( * ) Notice: Subject to any disclaimer, the term of this patent is extended or adjusted under 35 U.S.C. 154(b) by 295 days.

This patent is subject to a terminal disclaimer.

(21) Appl. No.: 14/234,815
(22) PCT Filed: Jul. 12, 2012
(86) PCT No.: PCT/FR2012/051665
§ 371 (c)(1),
(2), (4) Date: Jan. 24, 2014
(87) PCT Pub. No.: WO2013/017766
PCT Pub. Date: Feb. 7, 2013

(65) Prior Publication Data
US 2014/0150926 A1   Jun. 5, 2014

(30) Foreign Application Priority Data
Jul. 29, 2011 (FR) ...................................... 11 57008

(51) Int. Cl.
*B01L 1/02* (2006.01)
*G21F 7/005* (2006.01)
*C12M 1/12* (2006.01)

(52) U.S. Cl.
CPC ................ *B01L 1/02* (2013.01); *C12M 37/04* (2013.01); *G21F 7/005* (2013.01)

(58) Field of Classification Search
CPC ... G21F 7/005; B65B 61/06; B65B 69/0033; B01L 1/02
USPC .................... 141/383, 384, 98, 85, 329–330; 220/501; 414/412, 292, 217; 53/292, 53/133.3, 381.2
See application file for complete search history.

(56) References Cited

U.S. PATENT DOCUMENTS

| | | | |
|---|---|---|---|
| 5,853,207 A | 12/1998 | Saint martin et al. | |
| 6,553,722 B1 | 4/2003 | Porret et al. | |
| 8,919,830 B2 * | 12/2014 | Norton | B01L 1/02 292/143 |

FOREIGN PATENT DOCUMENTS

| | | |
|---|---|---|
| EP | 0 688 020 A1 | 12/1995 |
| EP | 1 141 974 A1 | 5/2004 |

(Continued)

OTHER PUBLICATIONS

International Search Report, dated Oct. 17, 2012, from corresponding PCT application.

*Primary Examiner* — Mark A Laurenzi
*Assistant Examiner* — Timothy P Kelly
(74) *Attorney, Agent, or Firm* — Young & Thompson

(57) ABSTRACT

A container for ensuring the transport and the aseptic transfer of a biopharmaceutical product from or to a closed chamber provided with a leaktight joining device, includes: an annular flange delimiting an opening, a removable cover, built-in elements for locking/unlocking the removable cover and a peripheral envelope. The built-in locking/unlocking elements include a built-in functional locking/unlocking arrangement formed by a through-housing formed in the annular flange and a blind housing formed in the removable cover, and by a pin at an inner radial position and a pin at an outer radial position. The container is capable of being in an initial locking position, in an intermediate unlocking position and in a final locking position owing to the displacements of the pin at an inner radial position and the pin at an outer radial position in the blind hole of the removable cover and in the through-housing of the annular flange.

23 Claims, 6 Drawing Sheets

(56) References Cited

FOREIGN PATENT DOCUMENTS

| FR | 2 721 289 A | 12/1995 |
| FR | 2 872 446 A1 | 1/2006 |
| GB | 2 102 719 A | 2/1983 |
| GB | 2 218 663 A | 11/1989 |
| WO | 2010/054031 A1 | 5/2010 |

* cited by examiner

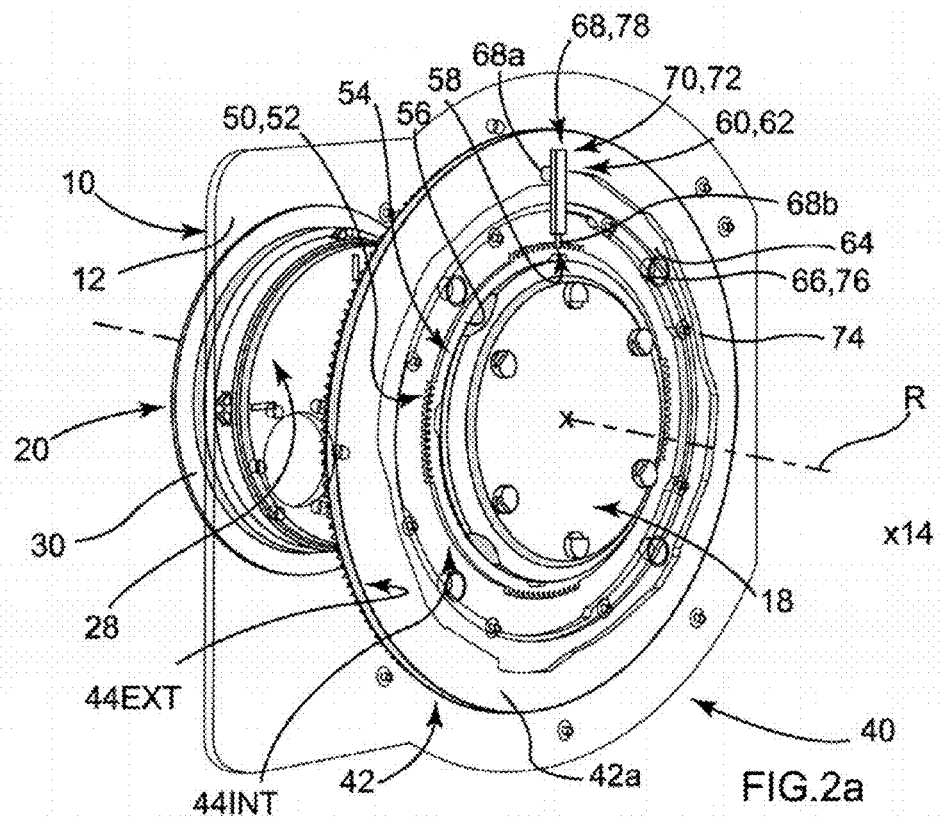
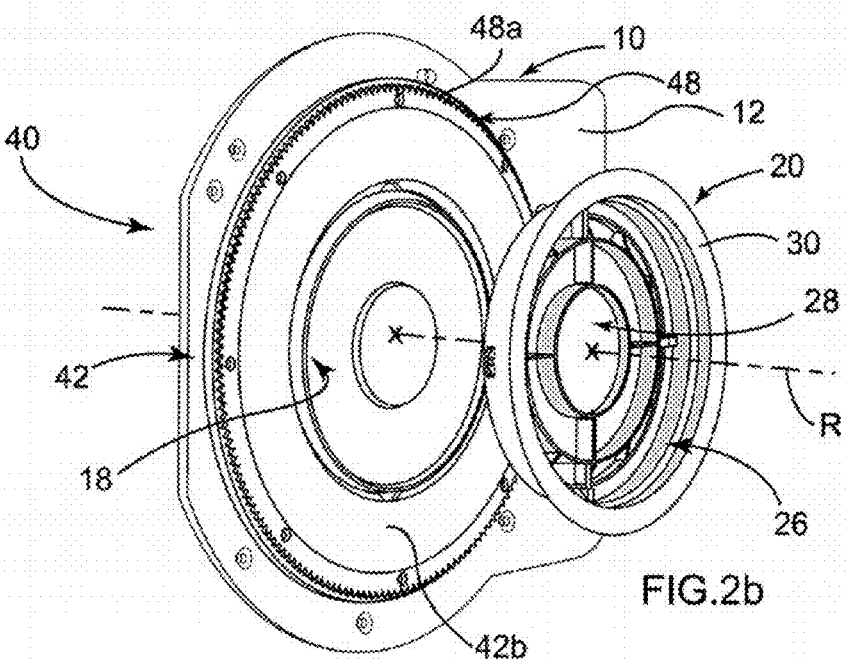

CONTAINER FOR THE ASEPTIC TRANSFER OF A BIOPHARMACEUTICAL PRODUCT

The invention relates to the field of the aseptic transfer of biopharmaceutical products between a container and a closed chamber.

More specifically, a first aspect of the invention concerns a container specially designed for the transport and the aseptic transfer of a biopharmaceutical product from or to an closed chamber. The invention also relates, in a second aspect, to an assembly comprising such a container, a closed chamber, and a leaktight joining device to ensure the aseptic transfer of biopharmaceutical products between the container and the closed chamber. The invention further relates, in a third aspect, to a method for the aseptic transfer of a biopharmaceutical product between the container and the closed chamber.

The term biopharmaceutical product or biopharmacy product is understood here to mean a product which is related to biotechnology, pharmacy, and more generally to the medical field. In particular, a biopharmaceutical product is a product obtained from biotechnology—culture media, cell cultures, buffers, artificial nutrition liquids—or a product intended to be used in the pharmaceutical or medical field, at least in part, as a solid more or less finely divided, as a liquid, or as a paste, or, more generally, a physical product—cap, container, integrated ports or tube, syringe, syringe plunger, functional processing or packaging means, a more or less complex assembly comprising a plurality of products, etc.—intended be used inside the closed chamber.

By convention, the terms "container" or "containing" mean that which, in biopharmacy, is able to and is designed for containing, enclosing, or holding in its interior a specific biopharmaceutical content or where appropriate several biopharmaceutical contents, in a static manner that is more or less lasting or permanent. Such biopharmaceutical contents typically consist of one or more biopharmaceutical product (s) as defined above. Such containers may be rigid or flexible, reusable or disposable, of various sizes, and are for example bags, sleeves, containers, vessels, bioreactors, or spouts for biopharmaceutical use, although this is not an exhaustive list.

In the field of aseptic transfers of biopharmaceutical products, there is a need for establishing a connection between a container and a fluid-tight chamber, in particular for the transfer of biopharmaceutical products, without breaking the seal of the container and/or chamber relative to the outside as this could result in contamination of the biopharmaceutical products.

To do this, disclosed in the prior art document EP-A1-0688020—in the preamble of Claim 1—is a container comprising an annular flange defining an opening, a removable door capable of sealing the flange, and built-in means for locking/unlocking the removable door against the flange, controlled by actuating means on a leaktight joining device associated therewith.

More specifically, the built-in locking/unlocking means comprise, firstly, a first arrangement formed by a through-hole passing through the flange and a blind hole extending within the thickness of the removable door and in line with the through-hole, as well as an internal pin and an external pin engaged one behind the other in these two holes. In this way, the container can change from an initial locking position where the internal pin is engaged with both the flange and the removable door, to an intermediate unlocking position where the ends of the internal and external pins facing each other are placed at the interface of the flange and the removable door, which allows separating the removable door from the flange.

The built-in locking/unlocking means comprise, secondly, a second arrangement that is structurally and functionally independent of the first, consisting of another through-hole passing through the flange, another blind hole extending within the thickness of the removable door and in line with the through-hole, as well as a pin engaged with the through-hole. The pin in question has a length that is greater than that of the through-hole so that it can be slid inside the blind hole to irreversibly lock the removable door on the annular flange.

This technical solution solves the general problem described above, to the extent that, when associated with the corresponding joining device, it allows the aseptic transfer of biopharmaceutical products between the closed chamber and the container. However, this implementation has a number of disadvantages.

First, the construction of two separate arrangements each comprising a through-hole in the annular flange to allow transitioning to the intermediate unlocked position and to the final locking position multiplies the areas of risk. By their very nature, the through-holes in the annular flange can be in contact with the environment outside the chamber and can be in contact with the environment inside the chamber. A defect in manufacturing or in the dimensions of the through-holes or associated pins can result in a loss of integrity leading to contamination of the biopharmaceutical products and/or the environment inside the closed chamber. This unreliability is admittedly limited but cannot be overlooked given the constraints of the field of biopharmaceutics.

In addition, this increase in the number of through-holes in the flange increases its bulk within the container structure, generates additional production costs, and complicates upgrading the handling systems to automated solutions that would improve the reliability of these systems.

Furthermore, the justification for this technical solution was that it uses a joining device equipped with a manual lever with two different directions of rotation for placing it in the intermediate unlocking position and the final locking position. Originally, such a technical solution facilitated the handling operations for operators since it allowed them first to move the lever in one direction to a stop position, for placing the container in the intermediate unlocking position, then to move it in the opposite direction to another stop position, for the final locking position. However, it has become apparent with use that this sequence of operations, combined with the use of an independent clamping system, was complex and not very intuitive and thus prone to errors.

Also known from the prior art of document EP-A1-1141974 is a container comprising built-in locking/unlocking means for the removable cover which, as is expressly stated in said document, are similar to those disclosed in document FR-A-2721289.

Firstly, the built-in locking/unlocking means allow unlocking the removable cover from the container by inserting two pins into coaxial holes made in the flange and the removable cover, until the contact area between these pins reaches the boundary between the through-hole arranged in the flange, and the blind hole made in the removable cover. Secondly, these built-in locking/unlocking means then lock the removable cover on the container by inserting another pin into other coaxial holes made in the flange and the removable cover.

Because of this similarity, the technical problems mentioned above are encountered in the same manner in the implementation and use of this container, and there is no need to describe them again.

Also known from the prior art of document WO-A1-2010/054031 is a container comprising an annular flange defining an opening, a removable cover capable of sealing the flange, and built-in means for locking/unlocking the removable cover against the flange, controlled by reversible actuating means carried directly on the container.

More specifically, the built-in locking/unlocking means are formed by several arrangements, each comprising a through-hole in the flange, a blind hole made in the removable cover, a pin able to enter through the through-hole in the flange and into the blind hole of the removable cover, and a lever able to control the movement of the pin in a reversible manner. The container is thus capable of offering only two alternative positions. In the first position, the locking position, where the removable cover is locked against the flange, the lever is lifted so that the pin simultaneously enters the through-hole in the flange and the blind hole of the removable cover, and the cover then forms a seal against the flange. In the second position, the unlocking position, where the cover is released, the lever is lowered so that the pin no longer passes beyond the through-hole of the flange which thus releases the removable cover from the flange.

This technical solution is different from those mentioned in documents EP-A1-1141974 and FR-A-2721289, in that it allows the operators to change the container in a reversible manner from a locking position to an unlocking position simply by manipulating levers arranged on the flange of the container. The container is thus reusable.

However, this arrangement also has disadvantages.

Due to the reversibility of the locking/unlocking and the accessibility of the actuating means—namely the levers—mounted directly on the flange of the container, the risk of unintentionally or accidentally opening containers filled with biopharmaceutical products is considerably increased. It is also possible for such containers to be initially open, thereby compromising the isolation of the biopharmaceutical products relative to the outside, as they are then closed and this breach in the containment cannot be identified.

Document WO2010/054031 discloses a container intended for the aseptic transfer of a product to a chamber. The container comprises an annular flange defining an opening and there is a removable cover provided.

Document GB 2,102,719 discloses a system for bringing hazardous materials in and out of an enclosure, such as a glovebox, through a port in a wall of the enclosure. The port is normally closed by a door which cooperates with a removable end closure on a container or the like when the latter is presented to and secured at the port. The container is secured in position at the port by means of a rotatable coupling ring. A locking device ensures that the door cannot be opened in the absence of a container at the port and also that the container cannot be removed from the port when the door is open. In place of the container, a glove secured to a rigid sleeve may be used to allow the operator to perform a work function within the glovebox.

Document FR 2872446 discloses a double-door leaktight transfer device for providing a fluid-tight seal between a first sealed chamber, for example a containment cell, and a second sealed chamber, for example a transfer box, comprising two doors each equipped with locking means for locking it to a flange having a central opening and an actuator for actuating the locking means, the actuators being rotatably mounted in the doors and comprising a peephole.

EP 0688020 discloses a leaktight joining device between two chambers isolated from an external environment and each equipped with a door capable of sealing an opening of the corresponding chamber delimited by an annular flange, each door being defined with an inside face in contact with the interior of the chamber and an outside face in contact with said external environment, said doors being provided with cooperating assembly means which allow applying them one against the other to create a seal, in order to mutually isolate their outside faces, wherein one of the two chambers is of the disposable type and comprises final locking means for its own door, controlled by first actuating means installed on the other chamber.

GB 2 218 663 discloses a double-lidded system comprising a first cylindrical container, open at one end, a first lid for the first container, means defining a port for a second container, and a second lid for said port, the first container having a peripheral seal for sealing to the port and to the first lid, and the second lid having a peripheral seal for sealing to the port and the first lid, wherein the first lid comprises a catch mechanism of a first rotary element for securing the first lid to the first container, the first container incorporating engagement means for cooperating with the catch mechanism of the first rotary element, the second lid incorporates a rotary drive shaft extending through it and means for rotating the shaft are provided, and a catch mechanism of the second rotary element which can be actuated by the shaft to secure the first lid to the second lid, the first lid comprising means with which the catch mechanism of the second rotary member can engage, the system lastly incorporating a clutch teeth mechanism with at least twenty teeth which are engaged when the first lid is adjacent to the second lid such that rotation of the shaft causes simultaneous rotation of the first and second rotary catch mechanisms.

In this context, the aim of the present invention is to provide a container specially intended for the transport and aseptic transfer of a product belonging to the biopharmaceutical field that is without at least one of the above limitations.

More particularly, the present invention relates to a container that is capable of such transfer without breaching its seal and which presents a limited number of at-risk areas, is simple to produce, and is intuitive to use in order to limit the risk of inadvertent or deliberate contamination.

For that purpose, a first aspect of the invention relates to a container specially designed for the transport and the aseptic transfer of a biopharmaceutical product to or from a closed chamber equipped with a leaktight joining device, comprising: an annular flange delimiting an opening; a removable cover adapted for sealing the opening of the annular flange; built-in means for locking/unlocking the removable cover on the annular flange; and a peripheral envelope integral with the annular flange and delimiting an enclosed inside space adapted for receiving products belonging to the biopharmaceutical field; wherein the built-in locking/unlocking means comprise at least one built-in functional locking/unlocking arrangement formed, on the one hand, by a through-housing formed in the annular flange and a blind housing formed in the removable cover and in the extension of the through-housing when the removable cover seals the opening of the annular flange, and, on the other hand, by a pin at an inner radial position and a pin at an outer radial position which can be introduced and moved within the blind housing of the removable cover and the through-housing of the annular flange; the container being able to be in an initial locking position where, on the one hand, the pin at an inner radial position has an internal functional portion for initial locking arranged in the blind housing of the removable cover and a external functional portion for initial locking arranged in the through-housing of the annular flange so as to prevent the relative movement of the removable cover with respect to the annular flange, and, on the other hand, the pin at an outer radial position is at least partially arranged in the through-housing of the annular flange; the container being able to be in an intermediate unlocking position in which, on the one hand, the pin at an inner radial position is at least partially arranged in the blind housing of the removable cover and is completely outside the through-housing of the annular flange, and, on the other hand, the pin at an outer radial position is at least partially arranged in the through-housing of the annular flange and is completely outside the blind housing of the removable cover so as to allow the relative movement of the removable cover with respect to the annular flange. More particularly, the container is characterized by its being able to be in a final locking position where, on the one hand, the pin at an inner radial position is arranged in the blind housing of the removable cover, and, on the other hand, the pin at an outer radial position has an internal functional portion for final locking arranged in the blind housing of the removable cover and an external functional portion for final locking arranged in the through-housing of the annular flange so as to prevent the relative movement of the removable cover with respect to the annular flange.

Such an embodiment avoids the use of two separate holes, in the annular flange and in the removable cover, changing to the intermediate unlocking position and to the final locking position. This limits the risk of leakage that can result from manufacturing or dimensional defects. Furthermore, the use of built-in functional locking/unlocking arrangements only requiring the movement of the pins along a single axis and in a single direction simplifies the mechanism for actuating the built-in locking/unlocking means, making it more intuitive to use while at the same time allowing automation of this process.

According to one embodiment, the through-housing and the pin at an outer radial position have lengths such that, when the built-in locking/unlocking means are in the initial locking position, said pin at an outer radial position has a functional end portion at the outer radial position which is either completely outside the through-housing, or is housed inside the through-housing, or is flush with the outer end opening of the through-housing.

Also according to one embodiment, the through-housing and the pin at an outer radial position have lengths such that, when the built-in locking/unlocking means are in the intermediate unlocking position, said pin at an outer radial position has a functional end portion at the outer radial position which is either completely outside the through-housing, or is housed inside the through-housing, or is flush with the outer end opening of the through-housing.

According to one embodiment, in addition, the through-housing and the pin at an outer radial position have lengths such that, when the built-in locking/unlocking means are in the final locking position, said pin at an outer radial position has a functional end portion at the outer radial position which is either completely outside the through-housing, or is housed inside the through-housing, or is flush with the outer end opening of the through-housing.

The fact that the pin at an outer radial position is completely outside the through-housing when the container is in the initial locking position or the intermediate unlocking position facilitates the operation of stationary locking/unlocking means consisting of causing the container to transition from the initial locking position to the intermediate unlocking position, or from the intermediate unlocking position to the final locking position. In effect, the pin at an outer radial position thus remains accessible without the radially movable pushing element having to move all the way inside the through-housing. Furthermore, the fact that this pin at an outer radial position is also completely outside the through-housing when the container is in the final locking position can be useful when it is necessary to disassemble or reopen the container after it has been placed in the final locking position, because the pin at an outer radial position is then more accessible than if it were positioned fully within the through-housing in the annular flange.

On the contrary: the fact that the pin at an outer radial position is positioned fully inside the through-housing when the container is in the initial locking position, the intermediate unlocking position, or the final locking position, allows limiting access to this pin at an outer radial position and therefore makes the inadvertent actuation of the built-in locking/unlocking means less probable and more complex. In addition, the transition to the final locking position becomes virtually irreversible. This option is advantageous, particularly when the container is disposable.

In addition, using the pin at an outer radial position so that it is flush with the outer end of the through-housing—in any of the initial locking, intermediate unlocking, or final locking positions—can restrict the introduction of stationary unlocking or locking means deep inside the through-housing while limiting access to this pin at an outer radial position, which reduces the risk of inadvertently opening the container.

In one embodiment, the pin at an inner radial position and the pin at an outer radial position have substantially identical lengths. This simplifies the procurement, production, and assembly of the inner and outer pins as it is then no longer necessary to distinguish the pins by their respective dimensions.

In one embodiment, the through-housing, the blind housing, the pin at an inner radial position, and the pin at an outer radial position are coaxial and oriented in a radial direction relative to the annular flange.

In an alternative embodiment, the blind housing, the pin at an inner radial position, and the pin at an outer radial position are coaxial and oriented in a direction forming an angle α with respect to a radial direction relative to the annular flange.

Moreover, according to one embodiment, the container also comprises built-in isolation and protection means arranged on an outer peripheral edge of the annular flange so as to obstruct the inadvertent manipulation of the built-in locking/unlocking means. These means can thus reduce the risk of inadvertent manipulation which could cause the container to transition from its initial locking position to the intermediate unlocking position, particularly during transport.

In this case, according to one embodiment, the built-in isolation and protection means comprise at least one built-in functional arrangement for isolation and protection, provided around the through-housing so as to obstruct the inadvertent manipulation of the pin at an outer radial position.

Thus, according to one embodiment, the built-in functional arrangement for isolation and protection has radial dimensions such that, in a temporary locking position, the pin at an outer radial position does not extend beyond said isolation and protection means.

In one embodiment, the built-in functional arrangement for isolation and protection comprises at least one lug, preferably two lugs, arranged around the through-housing of the annular flange.

In an alternative or additional embodiment, the isolation and protection arrangement may also comprise a bore formed in the annular flange and having a diameter greater than the diameter of the through-housing. This makes it more difficult to access the pin at an outer radial position but does not further complicate the movement of the latter by the stationary locking and unlocking means.

In one embodiment, the container further comprises built-in temporary clamping means arranged on an outer peripheral edge of the annular flange so as to allow temporarily clamping the container by preventing its axial movement on the closed chamber via actuation of the leaktight joining device.

In this case, according to one embodiment, the built-in temporary clamping means comprise at least one built-in functional arrangement for temporary clamping formed by at least one lug, preferably two lugs, having a built-in functional surface for axial clamping adapted to abut against a stationary functional surface for axial clamping, of the leaktight joining device, so as to prevent axial movement of the container relative to the closed chamber.

Furthermore, according to one embodiment, the built-in temporary clamping means are at least partly formed by the isolation and protection means, thereby simplifying and reducing the materials required for the container while lowering production costs.

In one embodiment, the built-in functional arrangement for temporary clamping and the built-in functional arrangement for isolation and protection are formed by at least one common lug, and preferably two common lugs.

In one embodiment, the built-in locking/unlocking means comprises n built-in functional arrangements for locking/unlocking, regularly distributed around the annular flange and the removable cover, with n greater than or equal to 1. This reinforces the initial and final locking of the removable cover against the annular flange.

In this case, according to one embodiment, the built-in isolation and protection means comprise n built-in functional arrangements for isolation and protection, regularly distributed around the annular flange and indexed relative to the n built-in functional arrangements for locking/unlocking.

In one embodiment, the built-in temporary clamping means comprise m built-in functional arrangements for temporary clamping, regularly distributed around the annular flange, with m greater than or equal to 1.

In this case, according to one embodiment, n is equal to m and the built-in functional arrangements for temporary clamping are indexed relative to the built-in functional arrangements for locking/unlocking.

In one embodiment, the container is disposable.

The invention also relates, in a second aspect, to an assembly comprising a chamber, a leaktight joining device, and a container as described above, for performing the aseptic transfer of a biopharmaceutical product between the chamber and the container.

In one embodiment, the chamber comprises a peripheral wall in which is arranged an opening sealed by a removable door, and the leaktight joining device comprises: stationary temporary clamping means able to keep the container clamped against the chamber so that the removable cover of said container is sealingly held against the door of said chamber; stationary unlocking means able to cause the container to transition from an initial locking position where the removable cover seals the container to an intermediate unlocking position where the removable cover is disengaged from the container and is sealingly held against the door of the chamber so as to ensure an aseptic communication between said container and said chamber; stationary locking means able to cause the container to transition from the intermediate unlocking position to a final locking position where said removable cover once again seals the container; an annular functional ring gear able to rotate about a geometric axis of rotation so as to actuate the stationary unlocking means and the stationary locking means of the container; the stationary temporary clamping means, the stationary unlocking means, and the stationary locking means being mechanically linked to the annular functional ring gear so that the one-way rotation of said annular functional ring gear about the geometric axis of rotation successively causes the actuation of the stationary temporary clamping means to hold the container in position against the chamber, then the actuation of the stationary unlocking means which causes the container to transition to the intermediate unlocking position, then the actuation of the stationary locking means of the container which causes the container to transition to the final locking position, and the actuation of the stationary temporary clamping means of the container which results in the release of the container.

Furthermore, according to a third aspect, the invention relates to a method for aseptic transfer intended to ensure the aseptic transfer of a biopharmaceutical product between a container and a chamber which are part of an assembly as described above, and comprises the successive steps of: having available the chamber, the leaktight joining device, and the container; positioning the container against the peripheral wall of the chamber; generating an axial clamping of the annular flange of the container against the peripheral wall of the chamber by one-way rotation of the annular functional ring gear; generating the transition of the container from the initial locking position to the intermediate unlocking position by one-way rotation of the annular functional ring gear, causing the movement of the pins at the inner and outer radial positions within the through-housing and blind housing; simultaneously opening the removable door of the chamber and the removable cover of the container, the removable cover being sealingly attached against the removable door; aseptically transferring one or more biopharmaceutical product(s) between the container and the chamber; simultaneously closing the removable door of the chamber and the removable cover of the container, the removable cover being sealingly attached against the removable door; generating the transition of the container from the intermediate unlocking position to the final locking position by one-way rotation of the annular functional ring gear which causes movement of the pins at the inner and outer radial positions within the through-housing and blind housing; generating the axial unclamping of the annular flange of the container relative to the peripheral wall of the chamber by one-way rotation of the annular functional ring gear.

Other features and advantages of the invention will become apparent from the description which is given below for informational purposes and which is non-limiting, with reference to the accompanying drawings, where:

FIGS. 2a and 2b are two general perspective views, from inside the chamber and from outside the chamber, of the leaktight joining device of FIG. 1 installed on a portion of the peripheral wall of the chamber and ready to be associated with the annular flange of a container according to the invention;

Figure 1:
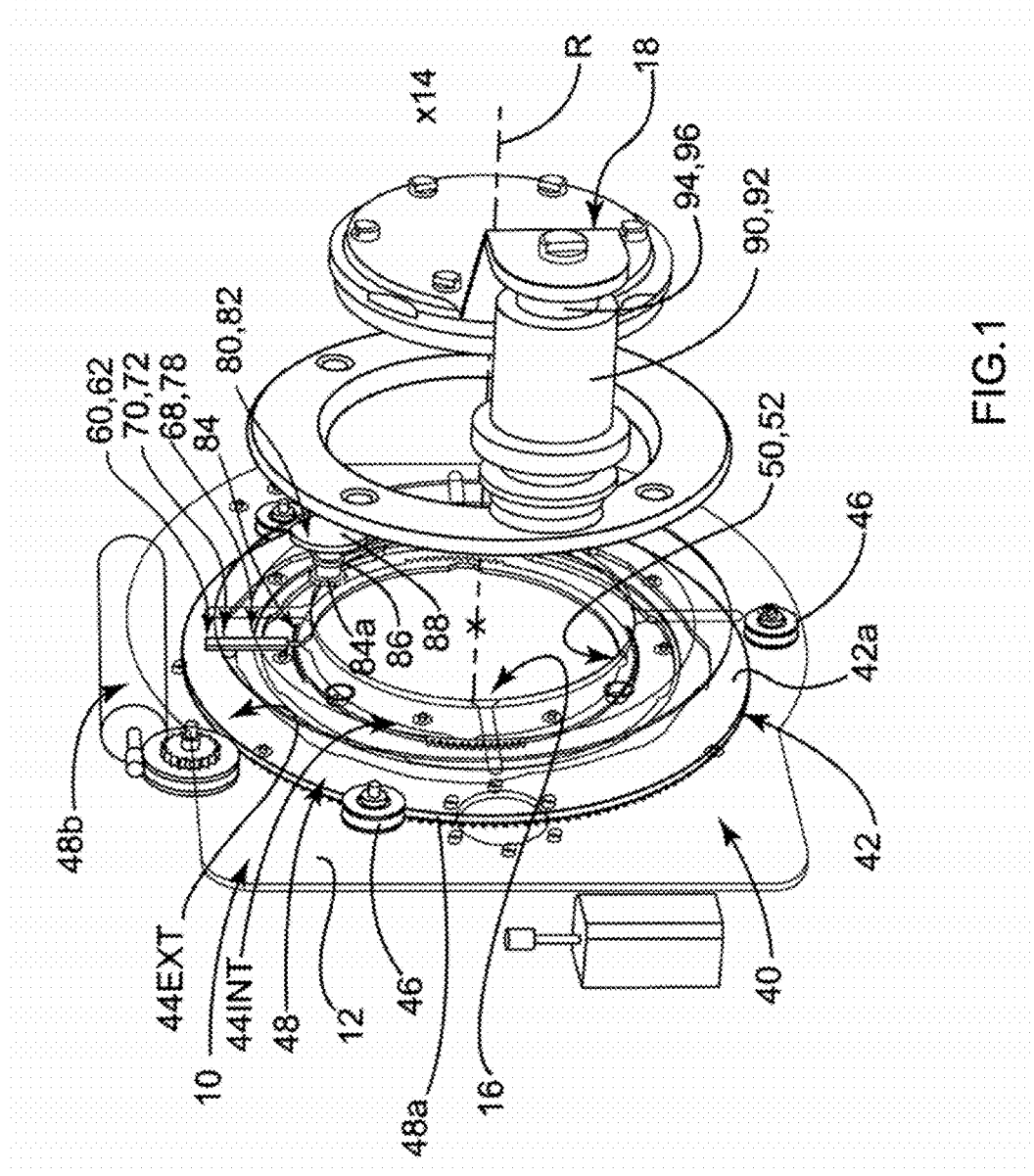
FIG. 1 is a general overview, showing an exploded perspective view of an embodiment of a leaktight joining device associated with the peripheral wall of a chamber.

FIG. 1 shows a closed chamber 10 comprising a peripheral wall 12 defining an enclosed inside space 14 and a circular opening 16 allowing the introduction of biopharmaceutical products (not shown) into the enclosed inside space 14.

The chamber 10—which can be an enclosed area or other analogous system—is designed to be permanently isolated from the outside environment. Thus, to avoid any loss of integrity and to maintain an aseptic environment within the inside space 14, the annular opening 16 is sealed by a removable door 18 positioned in the inside space and able to move from a closed position where the circular opening 16 is obstructed to an open position where the circular opening 16 is no longer obstructed.

By convention, the terms "internal" and "external" or "inner" and "outer" are used in the rest of this document to describe the relative positions of objects with respect to the geometric axis of the annular opening 16. Thus, objects described as "internal" or having an "inner radial position" should be regarded as positioned closest to the geometric axis of the annular opening 16, while objects described as "external" or having an "outer radial position" are to be considered as positioned farthest from the geometric axis of the annular opening 16.

FIGS. 2a and 2b show a container 20 intended for transporting biopharmaceutical products and ready to be associated with the closed chamber 10 in order to perform an aseptic transfer of biopharmaceutical products to or from the chamber 10.

For this purpose, the container 20 comprises a peripheral envelope (not shown) defining an enclosed inside space 24 into which the biopharmaceutical products can be introduced. The peripheral envelope also includes an annular opening 26 delimited by an annular flange 30 to which the peripheral envelope is integrally attached. The container 20 further comprises a removable cover 28 capable of sealing the opening 24 of the annular flange 30 by resting on a seal 22.

The container 20 can be realized according to different embodiments and, therefore, can have a peripheral envelope that is flexible and intended for a single use or rigid and intended to be reused after a decontamination procedure well known to those skilled in the art.

FIGS. 1, 2a and 2b illustrate an embodiment of a leaktight joining device 40.

This leaktight joining device 40 is intended to allow the aseptic transfer of biopharmaceutical products from the container 20 (described below) to the chamber 10. The object of the leaktight joining device 40 is therefore firstly to allow the assembly of the chamber 10 and the container 20, and then to allow placing the inside space 14 of this chamber 10 in temporary communication with the inside space of this container 20 in order to transfer biopharmaceutical products from one to the other, and lastly, to ensure the separation of said chamber 10 and said container 20.

These successive steps—encompassed below under the descriptor "aseptic transfer"—must be carried out without any communication between the outside environment and the inside spaces 14, 24 of the chamber 10 and of the container 20.

To do this, the leaktight joining device 40 according to the embodiment of FIG. 1 has a part formed outside the chamber 10 and supported by the peripheral wall 12—or by a supporting part distinct from the peripheral wall 12 but immovably attached to it—facing the annular opening 16. More specifically, the leaktight joining device 40 comprises an annular functional ring gear 42 having a face 42a oriented towards the peripheral wall 12 of the chamber 10 and a face 42b oriented towards the outside environment.

The annular functional ring gear 42 also has an inner peripheral edge $44_{INT}$ and an outer peripheral edge $44_{EXT}$ inscribed within three track rollers 46 which are supported by the external face of the peripheral wall 12. The annular functional ring gear 42 is thus positioned outside the chamber 10, which facilitates any maintenance operations. The three track rollers 46 form a track for the annular functional ring gear, and allow it to rotate about the geometric axis of the annular opening 16. It should be stressed, however, that the position of the annular functional ring gear could be maintained by some other similar mechanical element (bearing, etc.).

In the embodiment of FIG. 1, the annular functional ring gear 42, which presents several portions having different mechanical functions (described below), is formed as a single part—by machining, molding, or similar—from a single block of material. This embodiment has the advantage of simplifying the production of the annular functional ring gear, simultaneously reducing the production costs, and ensuring optimum positioning of the functional surfaces of the annular functional ring gear 42. However, it is understood that in other embodiments the annular functional ring gear may be formed from a plurality of discrete mechanical parts assembled together into one piece so that rotation of one of these mechanical parts around the geometric axis of rotation R causes the rotation of the whole.

It should be noted that, by convention, objects referred to as "stationary" are part of the leaktight joining device 40 and are therefore intended to be connected and permanently attached to the chamber 10. Conversely, objects referred to as "built-in" are intended to be supported by the containers 20 and therefore move with said containers.

Figure 3A:
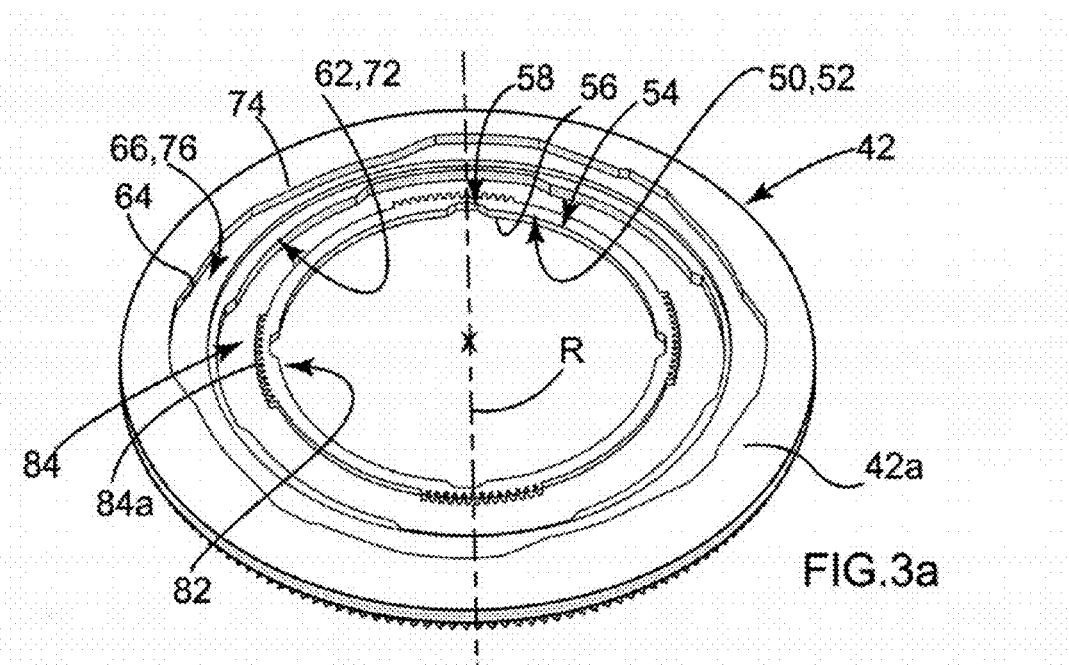
FIGS. 3a and 3b are two perspective detail views of the annular functional ring gear that is part of the embodiment of the joining device of FIG. 1.
Figure 3B:
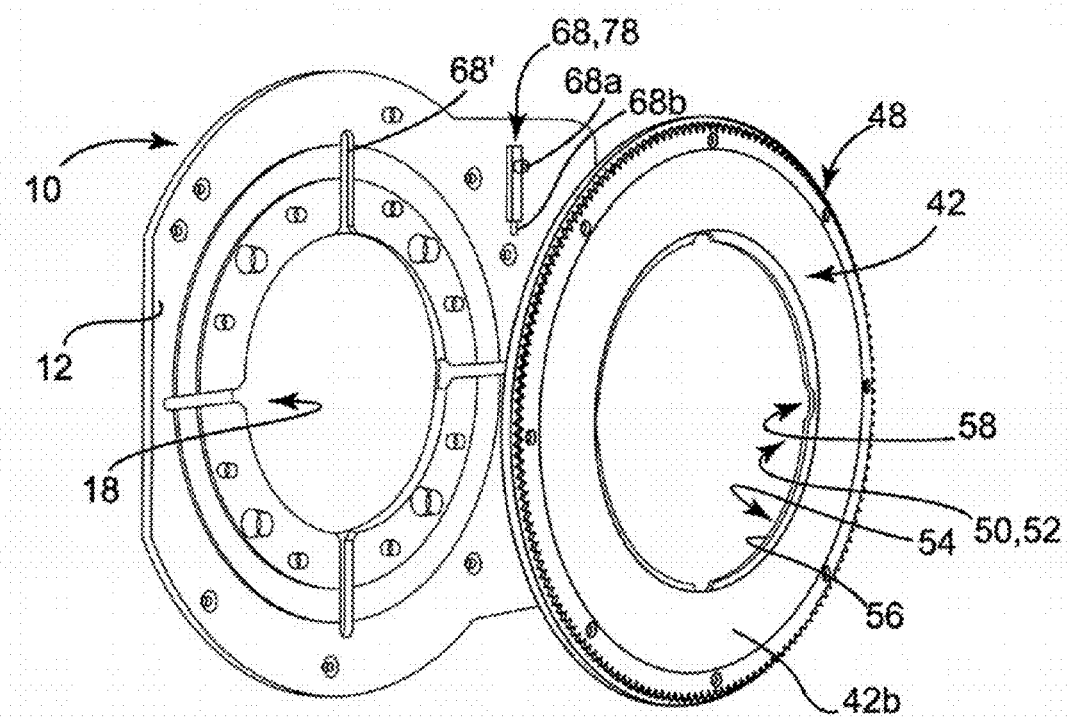

The annular functional ring gear 42, more particularly illustrated in FIGS. 3a and 3b, has a stationary rotary drive portion 48 arranged near the outer peripheral edge of the annular functional ring gear 42 and formed by radially oriented teeth 48a driven by a motor 48b, placed outside the chamber 10, or in an alternative embodiment, by a manually actuated lever (not shown). From the momentum of the motor 48b, the annular functional ring gear is able to begin a one-way rotation about the geometric axis of rotation R. By convention, the one-way rotation is considered below to be clockwise. However, the direction of rotation of the annular functional ring gear can alternatively correspond to the counterclockwise direction.

The leaktight joining device 40 comprises stationary temporary clamping means 50.

The stationary temporary clamping means 50 serve to keep the container 20 clamped against the chamber 10 so that the removable cover 28 of the container 20 is sealingly applied against the removable door 18 of the chamber 10.

These stationary temporary clamping means 50 are mechanically linked to the annular functional ring gear 42 so that the rotation of this annular functional ring gear 42 about the geometric axis of rotation R in the clockwise direction mechanically actuates the stationary temporary clamping means 50.

In the embodiment of FIG. 1, the stationary temporary clamping means 50 comprise four stationary functional arrangements for temporary clamping 52 regularly distributed around the annular functional ring gear 42. Each of these stationary functional arrangements for temporary clamping 52 is formed of a functional clamping ring portion 54 which is part of the annular ring 42. Each functional clamping ring portion 54 thus has a functional surface for axial clamping 56, and an opening 58 for inserting complementary built-in clamping means arranged on a portion of the outer periphery of the container (described later).

In the embodiment of FIG. 1, the functional surface for axial clamping 56 is formed on the inner peripheral edge 44$_{INT}$ of the annular functional ring gear 42 by an axially offset extension of the outer face of the peripheral wall 12 of the chamber 10, with regular interruptions forming the insertion opening 58. However, alternative embodiments for axially clamping the annular flange 30 of the container 20 against the outer face of the peripheral wall 12 of the chamber 10 could also be considered.

The leaktight joining device 40 comprises stationary unlocking means 60.

The stationary unlocking means 60 are intended for allowing the container 20 to transition from an initial locking position where the removable cover 28 seals the container 20, to an intermediate unlocking position where the removable cover 28 is detached from the container and sealingly applied against the door 18 of the chamber 10 so as to ensure an aseptic communication between the container 20 and the chamber 10.

As before, these stationary unlocking means 60 are mechanically linked to the annular functional ring gear 42 so that the clockwise rotation of this annular functional ring gear 42 about the geometric axis of rotation R mechanically actuates the unlocking means 60. However, in view of the arrangement of these stationary unlocking means 60 relative to the stationary temporary clamping means 50, the actuation of the stationary unlocking means 60 only occurs after the axial clamping of the container 20 against the chamber 10.

According to the embodiment of FIG. 1, also visible in FIGS. 3a and 3b, the stationary unlocking means 60 comprise several stationary functional unlocking arrangements 62—in this case four arrangements—regularly distributed around the annular functional ring gear 42.

Each of these stationary functional unlocking arrangements 62 firstly comprises a functional ring portion forming an inward- or outward-facing radial cam 64 which is part of the annular functional ring gear 42. In this case, the functional ring portion forming the radial cam 64 is created using a guideway 66 created in the annular functional ring gear 42 although this embodiment is not limiting.

Each of these stationary functional unlocking arrangements 62 secondly comprises a radially movable pushing element 68 able to cooperate with the functional ring portion forming the radial cam 64. In this way, during the rotation of the functional ring gear 42 to an intermediate unlocking position, the relative movement of the annular functional ring gear 42 with respect to the pushing element 68—which remains rotationally fixed as it is locked in a complementary arrangement 68'—causes movement of said pushing element 68 in the radial direction and causes the container 20 to transition from an initial locking position to an intermediate unlocking position (described later).

More particularly, according to the illustrative and non-limiting embodiment of FIG. 1, the pushing element 68 which is rotationally fixed relative to the peripheral wall 12 of the chamber 10, has in particular a roller 68a arranged in the guideway 66 and an activation pin 68b connected to the roller 68a so that the movement of this roller in the radial direction causes a radial movement of the activation pin 68b, until the container 20 transitions to the intermediate unlocking position.

It should be noted that the above phrase "movement in the radial direction" should be understood in its most general sense and can thus correspond to a line passing through the geometric axis of rotation R or slightly inclined and forming an angle α relative to the radial direction of the annular flange 30.

The leaktight joining device 40 comprises stationary locking means 70.

The stationary locking means 70 are intended for causing the container 20 to transition from the intermediate unlocking position to a final locking position where said removable cover 28 again seals the container 20.

As before, the stationary locking means 70 are mechanically linked to the annular functional ring gear 42 so that the clockwise rotation of this annular functional ring gear 42 about the geometric axis of rotation R mechanically actuates the stationary locking means 70. Similarly to the above, the relative position of the stationary locking means 70 and the stationary unlocking means 60 around the annular functional ring gear 42 is such that the actuation of these stationary locking means 70 can only occur after the stationary unlocking means 60 are stopped.

According to the embodiment of FIG. 1, visible in FIGS. 3a and 3b, the stationary locking means 70 comprise four stationary functional unlocking arrangements 72 regularly distributed around the annular functional ring gear 42.

Each of these stationary functional unlocking arrangements 72 firstly includes a functional ring portion forming an inward- or outward-facing radial cam 74 which is part of the annular functional ring gear 42. As before, this functional ring portion forming a radial cam 74 is based on a guideway 76 formed in the annular functional ring gear 42, although this embodiment is not limiting.

Each of these stationary functional unlocking arrangements 72 then comprises a radially movable pushing element 78, able to cooperate with the functional ring portion forming a radial cam 74. In this manner, when the functional ring gear 42 is rotated to a final locking position, the relative movement of the annular functional ring gear 42 with respect to the pushing element 78—which remains rotationally fixed because it is locked in a complementary arrangement 68'—causes said pushing element 78 to be moved in the radial direction and causes the container 20 to transition from the intermediate unlocking position to a final locking position (described below).

More particularly, according to the illustrative and non-limiting embodiment of FIG. 1, the pushing element 78 which is rotationally fixed relative to the peripheral wall 12 of the chamber 10 is the same as the pushing element 68 which is part of the stationary functional unlocking means 60. This pushing element 78 therefore comprises a roller 68a arranged in the guideway 76 and an activation pin 68b connected to the roller 68a so that the movement of said roller in the radial direction causes a radial movement of the activation pin 68b, until the container 20 is transitioned to the intermediate unlocking position.

It therefore follows that the functional ring portion forming a radial cam 74 of the stationary functional locking arrangement 72, is arranged in the extension of the functional ring portion forming a radial cam 64 of the stationary functional unlocking arrangement 62, considering the one-way rotation of the annular functional ring gear 42. In this regard, the ring portions forming a radial cam 72, 62 of the stationary functional locking arrangement 74 and of the stationary functional unlocking arrangement 62 are formed by a continuous guideway 66, 76 arranged in the annular functional ring gear 42, and the radially movable pushing element 68, 78 comprises a roller 68a arranged in the continuous guideway 66, 76 such that the rotation of the annular functional ring gear generates radial movement of the roller 68a which results in the corresponding displacement of an activation pin 38b.

Conversely, according to one alternative (not shown), the stationary unlocking means 60 and the stationary locking means 70 may optionally be structurally and functionally separate and independent of each other.

The leaktight joining device 40 comprises stationary retention/release means 80.

These stationary retention/release means 80 are intended to disable/enable the opening of the removable door 18 of the chamber 10 and are mechanically connected to the annular functional ring gear 42 such that the clockwise one-way rotation of this annular functional ring gear 42 about the geometric axis of rotation R mechanically actuates the stationary retention/release means 80. More particularly, because of the position of these stationary retention/release means 80 on the annular functional ring gear 42, these means ensure the release of the removable door 18 from the chamber 10. In the embodiment of FIG. 1, the stationary retention/release means 80 ensure the release of the removable door 18 after actuation of the stationary unlocking means 60 has caused the container 20 to transition to the intermediate unlocking position. In this manner, opening the removable door 18 of the chamber 10 is delayed indefinitely when a problem occurs during the intermediate unlocking of the container 20. This minimizes containment issues—which are necessarily more complex to rectify within the chamber 10—which could result from improper handling of the container 20. Similarly, these stationary retention/release means 80 are arranged on the annular functional ring gear 42 to ensure that the removable door 18 of the chamber 10 remains in place until the stationary locking means 70 have been activated in order to transition the container 20 to the final locking position.

According to another embodiment, it is also possible to arrange the stationary retention/release means 80 on the annular functional ring gear 42 so that these means release the removable door 18 simultaneously with the transition of the container 20 to the intermediate unlocking position, then block this removable door 18 simultaneously with the transition of the container 20 to the final locking position.

Finally, according to a third embodiment, it is conceivable to arrange the stationary retention/release means 80 on the annular functional ring gear 42 so that these means release the removable door 18 of the chamber 10 before the container 20 transitions to the intermediate unlocking position, and these means block the removable door 18 of the chamber 10 after the container 20 transitions to the final locking position.

The stationary retention/release means 80 as illustrated in FIG. 1 comprise at least one stationary functional arrangement for retention/release 82 formed by a functional ring portion forming gear teeth 84 which is part of the annular functional ring gear 42. As such, this functional ring portion forming gear teeth 84 is positioned outside the chamber 10.

Furthermore, in the embodiment of FIG. 1, this functional ring portion forming gear teeth 84 is notched so as to engage with a drive shaft 86 passing through the peripheral wall 12 of the chamber 10 and which drives a blocking member 88 during the one-way rotation of the functional ring gear. More particularly, the blocking member 88—which is located within the inside space 14 of the chamber 10—is arranged to be able to move from a blocked position where a covering portion 88a prevents the removable door 18 of the chamber 10 from opening, to a freed position where the covering portion 88a no longer prevents the removable door 18 from opening.

The leaktight joining device 40 also comprises stationary operating means 90.

These stationary operating means 90 are intended for opening the removable door 18 of the chamber 10 and for sealing it closed again.

To do this, the stationary operating means 90 may, according to a first embodiment (not shown), be driven mechanically by the annular functional ring gear 42. In this case, the stationary operating means 90 are mechanically connected to the annular functional ring gear 42 so that the clockwise one-way rotation of the annular functional ring gear 42 about the geometric axis of rotation R mechanically actuates the stationary operating means 90. More particularly, the position of these stationary operating means 90 on the annular functional ring gear 42 allows opening the removable door 18 of the chamber 10 after the container 20 transitions to the unlocking position, then closing the removable door 18 before the container 20 transitions to the final locking position.

In a second embodiment illustrated by FIG. 1, the stationary operating means 90 are driven by a motor 92 controlled by the displacement of the annular functional ring gear 42.

These stationary operating means 90 then comprise a rotational arm 94 adapted to rotate about a horizontal axis of rotation, as well as a translational arm 96 adapted to move along a horizontal axis. In this manner, the stationary operating means 90 allow, by means of the motor 92, moving the removable door 18 of the chamber 10, first in an axial direction, then in a direction substantially perpendicular to the axial direction so that the removable door 18 does not interfere with the passage of the biopharmaceutical product during the aseptic transfer between the chamber 10 and the container 20.

It should be noted that, according to the invention, the temporary stationary clamping means 50, the stationary unlocking means 60, the stationary locking means 70, and possibly the retention/release means 80 and the operating means 90, are mechanically linked to the annular functional ring gear 42 and arranged so that the clockwise one-way rotation of said annular functional ring gear 42 about the geometric axis of rotation R successively causes the actuation of the temporary stationary clamping means 50 to maintain the container 20 in position against the chamber 10, and then simultaneously or successively the actuation of the stationary unlocking means 60 which ensures the transition of the container 20 to the intermediate unlocking position and the actuation of the stationary retention/release means 80 which ensures the release of the removable door 18 of the chamber 10, then simultaneously or successively the actuation of the stationary retention/release means 80 which blocks the removable door 18 of the chamber 10 and the actuation of the stationary locking means 70 which ensures the transition of the container 20 to the final locking position, and once again the actuation of the temporary stationary clamping means 50 for the container in order to release the container 20.

Moreover, the temporary stationary clamping means 40 are arranged to ensure the positioning of the container 20 and an indexing relative to the other functional means. Similarly, the accumulation of several functional arrangements on the annular functional ring gear 42 allows completing a manipulation cycle of the container 20 with a 1/n rotation. In this current case, the embodiment comprises four distinct functional arrangements distributed regularly over the annular functional ring gear, but it would be possible to include less—one, two, or three—or to include more.

It should be noted that the one-way rotation of the annular functional ring gear 42 ensures the actuation of the temporary stationary clamping means, unlocking means, locking means, retention/release means, and operating means, which this annular functional ring gear moves in one direction of rotation or in the other.

Moreover, it is also possible to integrate this annular functional ring gear 42, not outside the chamber 10 as shown in the embodiment of FIG. 1 but directly in the inside space 14 of the chamber 10, against the inner face of the peripheral wall 12. This embodiment would avoid the use of retention/release means 80 having a drive shaft 86 passing through the peripheral wall 12.

Figure 4:
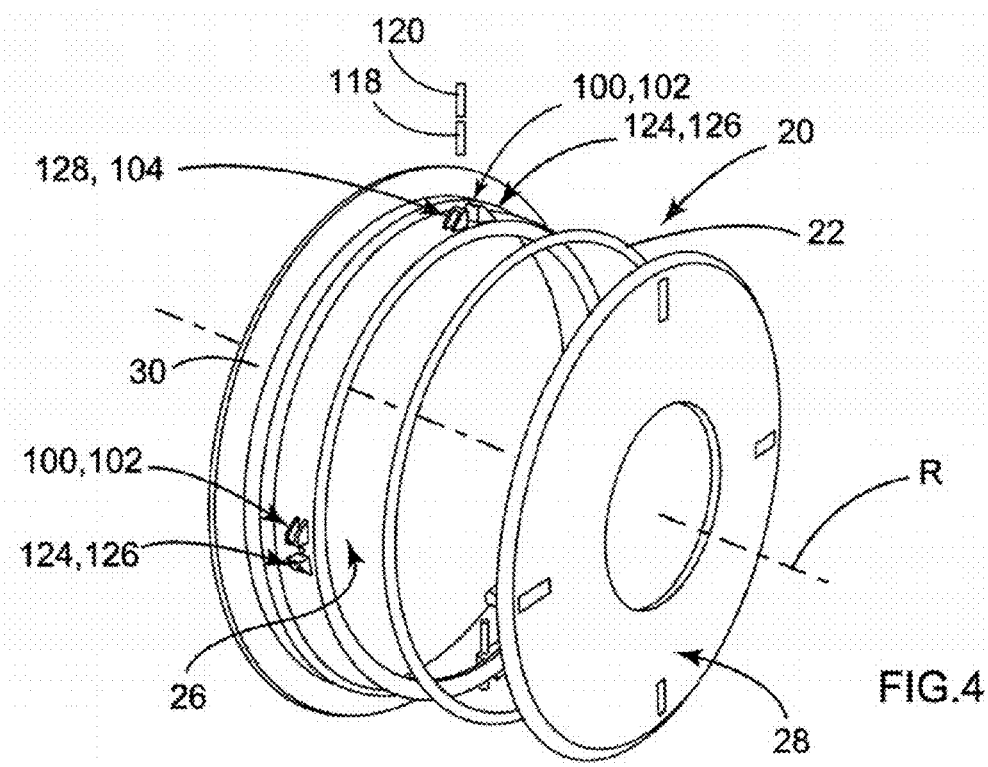
FIG. 4 is a general overview, showing an exploded perspective view of an embodiment of a container according to the invention where the peripheral envelope is not shown.

FIG. 4 shows details of an embodiment of a container intended to be associated with the leaktight joining device of the invention.

The peripheral envelope of the container 20 is not shown in this illustration, however.

As indicated above, this container 20 is intended for the transport and aseptic transfer of biopharmaceutical products to or from a chamber 10 equipped with the leaktight joining device 40 according to the invention.

For that purpose, the container 20 comprises the annular flange 30 delimiting the annular opening 26, the removable cover 28 adapted for sealing the opening 26 of the annular flange 30, and the peripheral envelope secured to the annular flange 30 and delimiting the enclosed inside space 24 for containing the biopharmaceutical products. In this manner, when closed by the removable cover 28, the container 20 is sealed, preventing any leakage or any introduction of material into the inside space 24. The container 20 may be rigid or flexible and reusable or disposable, depending on the case. By way of example and in no way limiting, it may be a container 20 of any size, such as a bag, a sleeve, a vessel, a bioreactor, a spout, etc.

The container 20 also comprises built-in temporary clamping means 100.

These built-in temporary clamping means 100 are arranged on an outer peripheral edge of the annular flange 30 in a manner that allows temporarily clamping the container 20 by axially locking it in place on the outside face of the peripheral wall 10 of the chamber 10 via the actuation of the leaktight joining device 40.

More particularly, according to the embodiment of FIG. 4, the built-in temporary clamping means 100 comprise at least a built-in functional arrangement for temporary clamping 102 formed by at least one lug 104, preferably two lugs 104, having a built-in functional surface for axial clamping 106 adapted to abut against the functional stationary surface for axial clamping 56 of the leaktight joining device 40. These lugs 104, which can be positioned between the outer face of the peripheral wall 12 of the chamber 10 and the stationary functional surface for axial clamping 56 of the leaktight joining device 40 by first passing through one of the openings 58 for introducing this leaktight joining device 40, allow blocking the axial movement of the container 20 relative to the chamber 10.

When the container 20 is clamped against the chamber 10, the removable cover 28 of the container 20 remains sealingly fixed—magnetically or by other means—against the removable door 108 of the chamber 10. In this manner, the outside space contained between the removable cover 28 and the removable door 18 cannot leak during the aseptic transfer.

The container 20 also includes built-in locking/unlocking means 110 for holding the removable cover 28 on the annular flange 30.

These built-in locking/unlocking means 110—their structure is detailed below—have the function of maintaining the container 20 in three distinct positions. The first position is referred to as the initial locking position because the locking/unlocking means 110 prevent relative movement of the removable cover 28 with respect to the annular flange 30. The second position, referred to as the intermediate unlocking position, occurs when the annular flange 30 of the container 20 is clamped axially against the peripheral wall 12 of the chamber 10 and allows relative movement of the removable cover 28 with respect to the annular flange 30. The third position, referred to as the final locking position, is assumed to take place after the aseptic transfer of biopharmaceutical products between the container 20 and the chamber 10 and prevents, irreversibly or again and reversibly, the relative movement of the removable cover 28 with respect to the annular flange 30.

To ensure this transition from the initial locking position to the intermediate unlocking position and then to the final locking position, the built-in locking/unlocking means 110 according to the embodiment of FIG. 4 include four built-in functional arrangements for locking/unlocking 112, regularly distributed around the annular flange 28 of the cover 30.

Each built-in functional arrangement for locking/unlocking 112 comprises a through-housing 114 formed in the annular flange 30 and a blind housing 116 formed in the removable cover 28 of the container 20 and in the extension of the through-housing 114.

Each built-in functional arrangement for locking/unlocking 112 also comprises a pin at an inner radial position 118 and a pin at an outer radial position 120. In the embodiment of FIG. 4, these two inner 118 and outer 120 pins have an elongated cylindrical body allowing them to be introduced and moved within the blind housing 116 formed in the removable cover 28 and the through-housing 114 arranged in the annular flange 30. It should be noted that the dimensional characteristics and the properties of the outer surface of these inner 118 and outer 120 pins are such that the pins can only be moved within the blind housing 116 and the through-housing 114 by gravity. In addition, these inner 118 and outer 120 pins could have a different body shape—for example, parallelepipedal—to achieve the same result.

In the embodiment of FIG. 4, the through-housing 114, the blind housing 116, the pin at an inner radial position 118, and the pin at an outer radial position 120 are coaxial and are aligned in a radial direction relative to the annular flange 30. More specifically, according to this embodiment, these elements extend in a substantially radial direction, oriented towards the geometric axis of rotation R. However, in an alternative embodiment, said through-housing 114, blind housing 116, pin at an inner radial position 118, and pin at an outer radial position 120 could also be oriented in a direction slightly inclined and forming an angle α with respect to a radial direction relative to the annular flange 30.

In the embodiment of FIG. 4, the blind housing 116 is flush with the through-housing 114, but there could also be a gap formed between the blind housing 116 and the through-housing 114 without this affecting the containment and handling of the container 20.

Figure 5A:
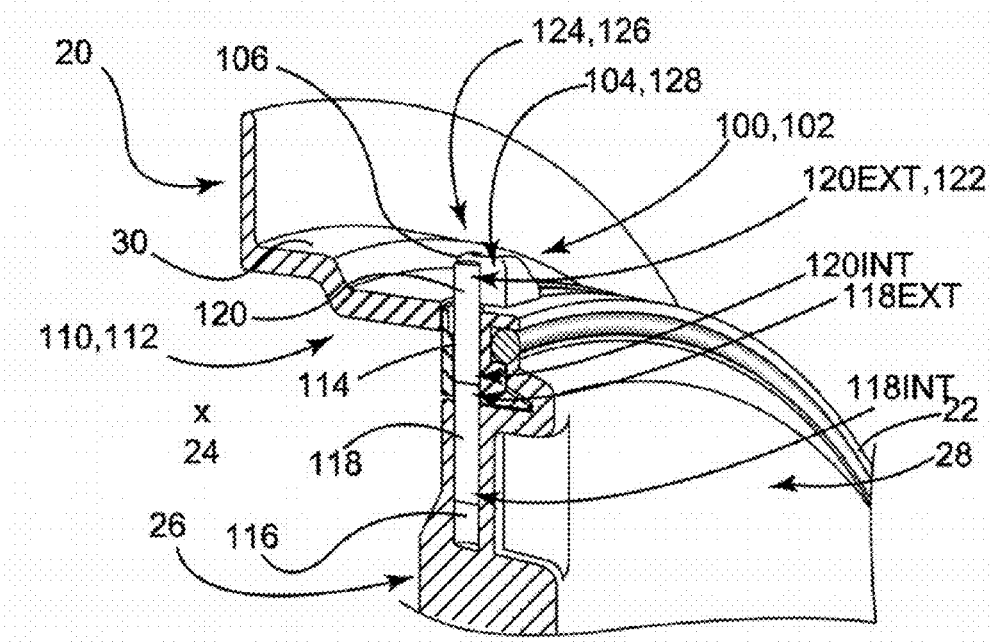
FIG. 5a is a cross-sectional detail view, showing a portion of the container of FIG. 4 in an initial locking position.

When the container 20 is in the initial locking position, as shown in FIG. 5a, the pin at an inner radial position 118 has an internal functional portion for initial locking $118_{INT}$ arranged in the blind housing 116 of the removable cover 28 and an external functional portion for initial locking $118_{EXT}$ arranged in the through-housing 114 of the annular flange 30. Thus, the pin at an inner radial position 118 prevents the relative movement of the removable cover 28 with respect to the annular flange 30.

Moreover, in this same initial locking position, the pin at an outer radial position 120 is at least partially arranged in the through-housing 114 of the annular flange 30. In a first embodiment (shown in FIG. 5a), the pin at an outer radial position 120 can then have a functional end portion at an outer radial position 122 that is not within the through-housing 114. This facilitates access to this functional end portion 122 by the stationary unlocking means 60 or locking means 70. In a second embodiment (not shown), this pin at an outer radial position 120 may alternatively have a functional end portion at an outer radial position 122 which is flush with the outer end opening of the through-housing 114. Access to this functional end portion 122 by the stationary unlocking means 60 or locking means 70 then remains relatively easy but the risk of inadvertently moving the pin at an outer radial position 120 is reduced. Finally, according to a third embodiment (not shown), said pin at an outer radial position 120 may have a functional end portion at an outer radial position 122 which is entirely housed within the through-housing 114. In this manner, it is virtually impossible to manipulate the pin at an outer radial position 120 without using a specific tool.

Figure 5B:
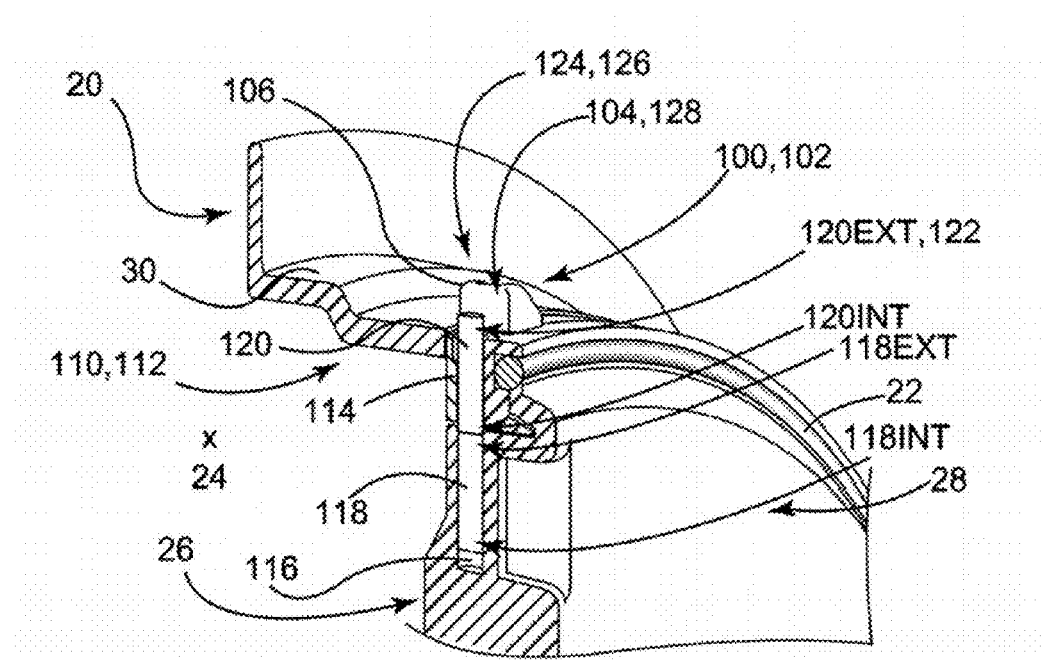
FIG. 5b is a cross-sectional detail view, showing a portion of the container of FIG. 4 in an intermediate unlocking position.

When the container 20 is in the intermediate unlocked position, as shown in FIG. 5b, the pin at an inner radial position 118 is at least partially arranged within the blind housing 116 of the removable cover 28 and is completely outside the through-housing 114 of the annular flange 30. In this manner, the pin at an inner radial position 118 no longer prevents the relative movement of the annular flange 30 and the removable cover 28 of the container 20.

In this intermediate unlocking position, the pin at an outer radial position 120 is at least partially arranged in the through-housing 114 of the annular flange 30 and is completely outside the blind housing 116 of the removable cover 28. In this manner, the pin at an outer radial position 120 has no more effect than the pin at an inner radial position 118 on the relative movement of the removable cover 28 with respect to the annular flange 30 which can therefore be separated to allow the aseptic transfer of biopharmaceutical products.

Similarly to the above, the functional end portion at an outer radial position 122 of said pin at an outer radial position 120 may either be completely outside the through-housing 114, or flush with the outer end opening of the through-housing 114, or be entirely housed within said through-housing 114.

Figure 5C:
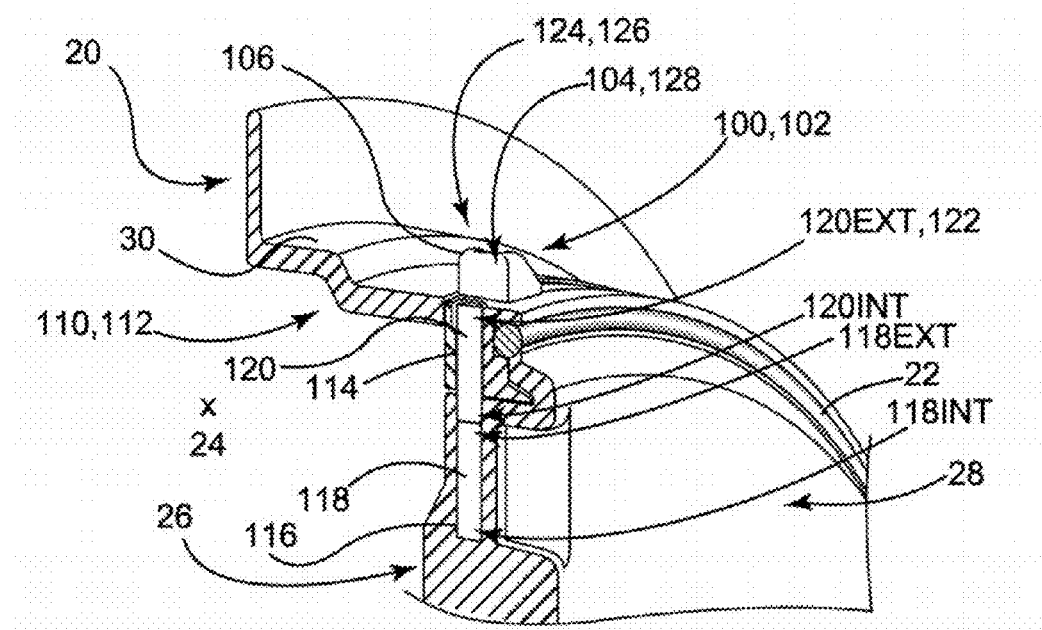
FIG. 5c is a cross-sectional detail view, showing a portion of the container of FIG. 4 in a final locking position.

Finally, to place the container 20 in the final locking position, as shown in FIG. 5c, it is first necessary to replace the removable cover 28 against the annular flange 30 and then place the built-in functional arrangement for locking/unlocking 112 in the appropriate position.

More particularly, in this position, the pin at an inner radial position 118 is positioned entirely within the blind housing 116 of the removable cover 28, while the pin at an outer radial position 120 has an internal functional portion for final locking $120_{INT}$ arranged in the blind housing 116 of the removable cover 28 and an external functional portion for final locking $120_{EXT}$ arranged in the through-housing 114 of the annular flange 30. Therefore, the blind housing 116 of the removable cover 28 has a length sufficient to accommodate the pin at an inner radial position 118 on the one hand, and the internal functional portion for final locking $120_{INT}$ on the other hand. Thus, the pin at an outer radial position 120 prevents the relative movement of the removable cover 28 with respect to the annular flange 30.

Again, the functional end portion 122 at an outer radial position of said pin at an outer radial position 120 may then be completely outside the through-housing 114 in order to facilitate any subsequent reopening of the container 20. Conversely, said functional end portion 122 at an outer radial position may be flush with the external end opening of the through-housing 114 or may be housed entirely within said through-housing 114 to limit the subsequent risk of opening the container 20.

Such use of pins at inner and outer radial positions 118, 120 to place the container in the initial locking, intermediate unlocking, and final locking positions makes it possible to have only one blind housing 116 and through-housing 114 in the removable cover 28 and the annular flange 30 per built-in functional arrangement for locking/unlocking 112, which limits the risk of contamination due to production defects. In addition, manipulation of the locking/unlocking means 110 is facilitated, as it is sufficient to move the inner and outer pins 118, 120 in a single direction in order to transition the container 20 successively from the initial locking position to the intermediate unlocking position, and then to the final locking position. The construction and operation of the leaktight joining device are thus simplified.

It should be noted that in the embodiment of FIG. 4, the pins at inner and outer radial positions 118, 120 have identical lengths, which simplifies the production and assembly of the pins at inner and outer radial positions 118, 120 on the container since it is then unnecessary to distinguish the pins according to their dimensions. Alternatively, these pins at inner and outer radial positions 118, 120 could have different lengths.

It should also be noted that the through-housing 114 and the pin at an outer radial position 120 have lengths such that, when the built-in locking/unlocking means 110 are in the provisional unlocking position, the pin at an outer radial position 120 has a functional end portion 122 at an outer radial position which is completely outside the through-housing 114. This facilitates the operation carried out by the stationary locking means 70 for transitioning the container 20 from the intermediate unlocking position to the final locking position because the pin at an outer radial position 120 is accessible without the radially movable pushing element 78 having to move all the way to the inside of the through-housing 114.

However, the lengths of the pin at an outer radial position 120 and of the through-housing 114 are such that, when the built-in locking/unlocking means 110 are in the final locking position, said pin at an outer radial position 120 has a functional end portion 120 at an outer radial position that is housed within the through-housing. When the container is placed in the final locking position, it then becomes complex and impractical without a suitable gripping tool to grasp the pin at an outer radial position 120. This raises the level of security relating to the fluid-tightness of the container 20 in the final locking position.

It would also be possible to integrate complementary protection and warning means—formed for example by complementary abutments or any similar element—on the pin at an outer radial position 120 and on the through-housing 114, preventing the removal of the pin at an outer radial position 120 from the housing 114 after the container 20 has transitioned to the final locking position and causing the destruction of a portion of the annular flange 30 in the event of such removal.

Alternatively (not shown), it is also possible for the lengths of the pin at an outer radial position 120 and of the through-housing 114 to be such that, when the built-in locking/unlocking means 110 are in the final locking position, said pin at an outer radial position 120 has a functional external end at an outer radial position that is completely outside the through-housing.

Such an embodiment would, however, facilitate the removal of the pin at an outer radial position 120 from the through-housing 114 and would provide a container that is reusable after being in the final locking position.

According to the embodiment of FIG. 4, the container 20 also includes built-in isolation and protection means 124.

The built-in isolation and protection means 124 are arranged on an outer peripheral portion of the annular flange 30 so as prevent inadvertent manipulation of the built-in locking/unlocking means supported by the annular flange 30.

In one embodiment, the built-in isolation and protection means 124 include four built-in functional arrangements for isolation and protection 126 placed around the four through-housings 114 so as to prevent inadvertent or deliberate manipulation of the pin at an outer radial position 120 when said pin is not fully inserted into the through-housing 118 in the annular flange 30.

Each built-in functional arrangement for isolation and protection 126 is based on two lugs 128, arranged around or on either side of the through-housing 114. In this embodiment, the lugs 128 have radial dimensions such that, in the temporary locking position, the pin at an outer radial position 120 does not extend beyond the lugs 128 constituting the isolation and protection means.

However, in an alternative or additional embodiment, the built-in functional arrangement for isolation and protection 62 could be based on a bore formed in the annular flange 30, radially oriented and having a diameter greater than the diameter of the through-housing 114. Such an embodiment would prevent access to the outer pin 120 while maintaining the space around this outer pin 120 in order to avoid complicating the operation of moving said pin by the stationary locking means 60 and unlocking means 70.

It should be noted that in the embodiment of FIG. 4, the lugs 104 forming the built-in temporary clamping means 102 and the lugs 128 forming the built-in isolation and protection means 124 are the same. These lugs 104, 108 therefore have, on the one hand, a built-in functional surface for axial clamping 56 ensuring the clamping of the container against the peripheral wall 12 of the chamber 10, and on the other hand a shape which protects and isolates the outer pin 120 when it is only partially inserted into the through-housing 114. Such an embodiment can reduce production costs and simplify the annular flange 30 by limiting the number of lugs to be created on the outer peripheral edge of the annular flange 30.

However, it would also be conceivable to use built-in temporary clamping means 102 and built-in isolation and protection means 124 that are structurally and functionally independent of each other, for example using some lugs 104 for the axial clamping and other different lugs for the isolation and protection of the outer pin 120.

It should be noted that similarly to the above, the built-in temporary clamping means 100 are arranged so as to index the position of the container 20 relative to the other stationary means that are part of the leaktight joining device 40. This accumulation of functional arrangements on the annular functional ring gear 42 allows completing a manipulation cycle of the container 20 with only a 1/n revolution of the annular functional ring gear 42. In the current case, the embodiment comprises four distinct functional arrangements distributed evenly around the annular functional ring gear 42, but it would be possible to include less—one, two, or three—or to include more.

Figure 6:
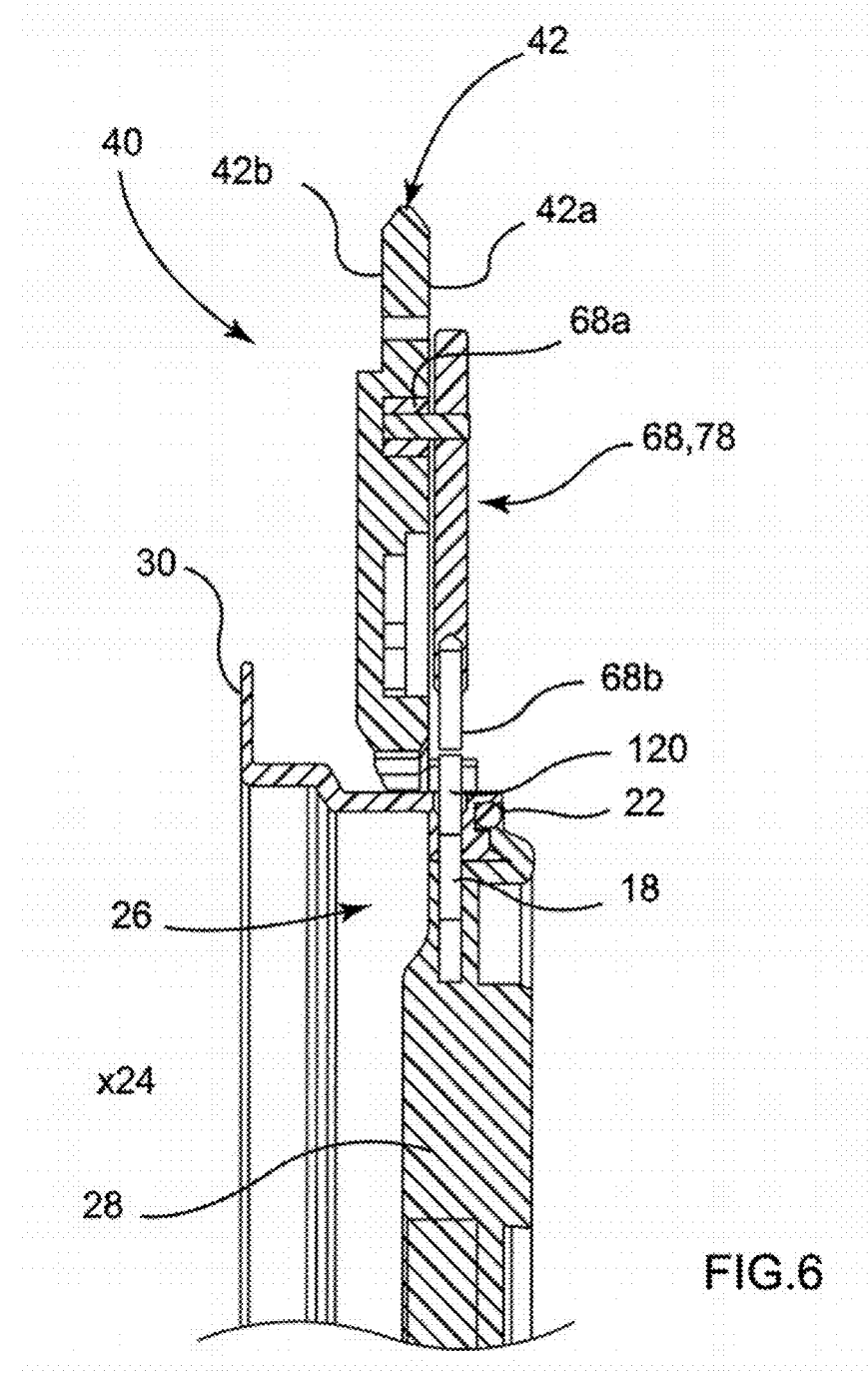
FIG. 6 is a cross-sectional detailed representation of an assembly comprising a closed chamber, a leaktight joining device, and a container according to the invention associated with the leaktight joining device and in the initial locking position.

The implementation of the aseptic transfer method of the invention will now be described in detail, with reference to FIG. 6.

This aseptic transfer method first consists of having a closed chamber 10 as described above and supporting a leaktight joining device 40 of the invention. Then this aseptic transfer method consists of having a container 20 in the initial locking position as described above.

The aseptic transfer method next involves placing the container 20 against the peripheral wall 12 of the chamber 10, introducing the lugs 104 that are part of the built-in functional arrangements for temporary clamping 102 through the insertion openings 58 that are part of the stationary temporary clamping means 50.

By doing so, the annular flange 30 of the container 20 comes into position against the peripheral wall 12 of the chamber 10 and the removable cover 28—at least partially formed of ferrite—is sealingly held against the outer face of the removable door 18—at least partially magnetized.

The aseptic transfer method then consists of generating the clockwise rotation of the annular functional ring gear 42 so that the functional ring portions acting as clamp 54 are positioned facing the lugs 104 forming the built-in temporary clamping means and trap these lugs 104 between the peripheral wall 12 of the chamber 10 and the axially clamping functional surfaces 56.

The container 20 is thus held in position by the leaktight joining device 40 against the circumferential wall 12 of the chamber 10.

The aseptic transfer method then consists of generating the clockwise rotation of the annular functional ring gear 42 to actuate the stationary unlocking means 60. More particularly, the clockwise rotation of this annular functional ring gear 42 generates a movement of the radially moveable pushing element 68 due to the change in radial position of the roller 68a in the guideway 66. The activation pin 68b then lowers and pushes the pin at an outer radial position 120 and the pin at an inner radial position 118 at the same time.

Following this operation, the pin at an inner radial position 118 is arranged in the blind housing 116 of the removable cover 28 and is completely outside the through-housing 114 in the annular flange 30, and the pin at an outer radial position 120 is arranged in the through-housing 114 in the annular flange 30 and is completely outside the blind housing 116 in the removable cover 28. The container 20 is thus in the intermediate unlocking position and the relative movement of the removable cover 28 with respect to the annular flange 30 is possible.

The aseptic transfer method also consists of, simultaneous with or successive to the preceding step, generating the clockwise rotation of the annular functional ring gear 42 to actuate the stationary retaining/release means 80 in order to release the removable door 18 of the chamber 10.

To this end, the functional ring portions forming gear teeth 84—which are rotationally driven with the annular functional ring gear 42—mesh with the drive shaft 86 and therefore with the blocking member 88 so that the latter no longer covers the outer face of the removable door 18 of the chamber 10. The removable door 18 can then be freely manipulated.

The aseptic transfer method then consists of causing the stationary operating means 90 to drive the removable door 18 of the chamber 10 and the removable cover of the container so as to free the annular openings 16, 26 of the chamber 10 and of the container 20.

To do this, the stationary operating means 90—which can be actuated by the annular functional ring gear 42 or by a motor controlled by the position of the annular functional ring gear 42—first drive the removable door 18 of the chamber 10 in a horizontal translation and then in a rotation about a horizontal axis.

As the container 20 is in the intermediate unlocking position, the removable cover 28 can be moved relative to the annular flange 30 and can follow the movements of the removable door 18 of the chamber 10 due to the magnetic force connecting them together. Thus, the chamber 10 and the container 20 are open to each other while being hermetically isolated from the outside environment.

The aseptic transfer of biopharmaceutical products between the container 20 and the chamber 10 can then occur.

The aseptic transfer method then consists of again driving the stationary operating means 90 so that the annular openings 16, 26 of the chamber 10 and of the container 20 are once again sealed closed.

As above, the stationary operating means 90 drive the removable door 18 of the chamber 10 and the removable cover of the container 20 in a rotation about a horizontal axis and then in a horizontal translation to return them to the same position as before.

The chamber 10 is then once again sealed by the removable door 18, relative to the outside and to the container 10. Symmetrically, the container 20 is sealed by the removable cover, relative to the outside and to the chamber 10.

The aseptic transfer method then consists of generating the clockwise rotation of the annular functional ring gear 42 to actuate the stationary retention/release means 80 in order to prevent movement of the removable door 18 of the chamber 10.

To this end, the functional ring portions forming gear teeth 84—which rotate with the annular functional ring gear 42—engage the drive shaft 86 and thus the blocking member 88, so that said blocking member once again covers the outer face of the removable door 18 of the chamber 10. The removable door 18 can then no longer be freely manipulated.

The aseptic transfer method consists, simultaneously with or successive to the previous step, of generating the clockwise rotation of the annular functional ring gear 42 in order to actuate the stationary locking means 70. More particularly, the clockwise rotation of this annular functional ring gear 42 generates a movement of the radially movable pushing element 78 due to the change of radial position of the roller 68a in the guideway 76. The activation pin 68b then lowers and pushes against the pin at an outer radial position 120 and the pin at an inner radial position 118 at the same time.

Following this operation, the pin at an inner radial position 118 is arranged within the blind housing 116 of the removable cover 28 while the pin at an outer radial position 120 has an internal functional portion for final locking $120_{INT}$ arranged within the blind housing 116 of the removable cover 28 and an outer functional portion for final locking $120_{EXT}$ arranged within the through-housing 114 in the annular flange 30. Relative movement of the removable cover 28 with respect to the annular flange 30 is therefore impossible and the container is then in the final locking position.

The aseptic transfer method then consists of generating the clockwise rotation of the annular functional ring gear 42 in order for the functional ring portions acting as temporary clamp 54 to be positioned so the insertion openings 58 are facing the lugs 104 forming the built-in temporary clamping means and free them.

The container 20 in the final locking position can thus be freely removed from the leaktight sealing device 40.

The invention claimed is:

1. A container (20) specially intended for the transport and the aseptic transfer of a biopharmaceutical product to or from a closed chamber (10) equipped with a leaktight joining device (40), comprising:
   an annular flange (30) delimiting an opening (26);
   a removable cover (28) adapted for sealing the opening (26) of the annular flange (30);
   built-in locking/unlocking means for locking/unlocking (110) the removable cover (28) on the annular flange (30);
   a peripheral envelope (22) integral with the annular flange (30) and delimiting an enclosed inside space (24) adapted for receiving products belonging to the biopharmaceutical field;
   wherein the built-in locking/unlocking means (110) comprise at least one built-in functional locking/unlocking arrangement (112) formed, on the one hand, by a through-housing (114) formed in the annular flange (30) and a blind housing (116) formed in the removable cover (28) and in an extension of the through-housing (114) when the removable cover (28) seals the opening of the annular flange (30), and, on the other hand, by a pin at an inner radial position (118) and a pin at an outer radial position (120) which can be introduced and moved within the blind housing (116) of the removable cover (28) and the through-housing (114) of the annular flange (30);
   the container (20) being able to be in an initial locking position where, on the one hand, the pin at the inner radial position (118) has an internal functional portion for initial locking ($118_{INT}$) arranged in the blind housing (116) of the removable cover (28) and an external functional portion for initial locking ($118_{EXT}$) arranged in the through-housing (114) of the annular flange (30)

so as to prevent the relative movement of the removable cover (28) with respect to the annular flange (30), and, on the other hand, the pin at the outer radial position (120) is at least partially arranged in the through-housing (114) of the annular flange (30);

the container (20) being able to be in an intermediate unlocking position in which, on the one hand, the pin at the inner radial position (118) is at least partially arranged in the blind housing (116) of the removable cover (28) and is completely outside the through-housing (114) of the annular flange (30) and, on the other hand, the pin at the outer radial position (120) is at least partially arranged in the through-housing (114) of the annular flange (30) and is completely outside the blind housing (116) of the removable cover (28) so as to allow the relative movement of the removable cover (28) with respect to the annular flange (30);

wherein the container (20) is able to be in a final locking position where, on the one hand, the pin at the inner radial position (118) is arranged in the blind housing (116) of the removable cover (28), and, on the other hand, the pin at the outer radial position (120) has an internal functional portion for final locking ($120_{INT}$) arranged in the blind housing (116) of the removable cover (28) and an external functional portion for final locking ($120_{EXT}$) arranged in the through-housing (114) of the annular flange (30) so as to prevent the relative movement of the removable cover (28) with respect to the annular flange (30); and built-in isolation and protection means (124) arranged on an outer peripheral edge of the annular flange (30) so as to obstruct an inadvertent manipulation of the built-in locking/unlocking means (110).

2. Container (20) according to claim 1, wherein the through-housing (114) and the pin at the outer radial position (120) have lengths such that, when the container (20) is in the initial locking position, said pin at the outer radial position (120) has a functional end portion at the outer radial position (122) which is either completely outside the through-housing (114), or is housed inside the through-housing (114), or is flush with the outer end opening of the through-housing (114).

3. Container (20) according to claim 1, wherein the through-housing (114) and the pin at the outer radial position (120) have lengths such that, when the container (20) is in the intermediate unlocking position, said pin at the outer radial position (120) has a functional end portion at the outer radial position (122) which is either completely outside the through-housing (114), or is housed inside the through-housing (114), or is flush with the outer end opening of the through-housing (114).

4. Container (20) according to claim 1, wherein the through-housing (114) and the pin at the outer radial position (120) have lengths such that, when the container (20) is in the final locking position, said pin at the outer radial position (120) has a functional end portion at the outer radial position (122) which is either completely outside the through-housing (114), or is housed inside the through-housing (114), or is flush with the outer end opening of the through-housing (114).

5. Container (20) according to claim 1, wherein the pin at the inner radial position (118) and pin at the outer radial position (120) have substantially identical lengths.

6. Container (20) according to claim 1, wherein the through-housing (114), the blind housing (116), the pin at the inner radial position (118), and the pin at the outer radial position (120) are coaxial and oriented in a radial direction relative to the annular flange (30).

7. Container (20) according to claim 1, wherein the through-housing (114), the blind housing (116), the pin at the inner radial position, and the pin at the outer radial position (120) are coaxial and oriented in a direction forming an angle α with respect to a radial direction relative to the annular flange (30).

8. Container (20) according to claim 1, wherein the built-in isolation and protection means (124) comprise at least one built-in functional arrangement for isolation and protection (126), provided around the through-housing (114) so as to obstruct an advertent manipulation of the pin at the outer radial position (120).

9. Container (20) according to claim 8, wherein the built-in functional arrangement for isolation and protection (126) has radial dimensions such that, in a temporary locking position, the pin at the outer radial position (120) does not extend beyond said isolation and protection means (124).

10. Container (20) according to claim 8, wherein the built-in arrangement for functional isolation and protection (126) comprises at least one lug (128) arranged around the through-housing (114) of the annular flange (30).

11. Container (20) according to claim 8, wherein the isolation and protection arrangement (126) comprises a bore formed in the annular flange (30) and having a diameter greater than the diameter of the through-housing (114).

12. Container (20) according to claim 1, comprising built-in temporary clamping means (100) arranged on an outer peripheral edge of the annular flange (30) so as to allow temporarily clamping the container (20) by preventing axial movement on the closed chamber (10) via actuation of the leaktight joining device (40).

13. Container (20) according to claim 12, wherein the built-in temporary clamping means (100) comprise at least one built-in functional arrangement for temporary clamping (102) formed by at least one lug (104) having a built-in functional surface for axial clamping (106) adapted to abut against a stationary functional surface for axial clamping (56), of the leaktight joining device (40), so as to prevent axial movement of the container (20) relative to the chamber (10).

14. Container (20) according to claim 13 comprising built-in isolation and protection means (124) arranged on an outer peripheral edge of the annular flange (30) so as to obstruct an inadvertent manipulation of the built-in locking/unlocking means (110), wherein the built-in temporary clamping means (100) are at least partly formed by the isolation and protection means (124).

15. Container (20) according to claim 14, wherein the built-in functional arrangement for temporary clamping (102) and the built-in functional arrangement for isolation and protection (126) are formed by at least one common lug (104, 128).

16. Container (20) according to claim 1, wherein the at least one built-in functional locking/unlocking arrangement comprises n built-in functional arrangements for locking/unlocking (112), regularly distributed around the annular flange (30) and the removable cover (28), with n greater than or equal to 1.

17. Container (20) according to claim 16, wherein the built-in isolation and protection means (124) comprise n built-in functional arrangements for isolation and protection (126), regularly distributed around the annular flange (30) and indexed relative to the n built-in functional arrangements for locking/unlocking (112).

18. Container (20) according to claim 13, wherein the built-in temporary clamping means (100) comprise m built-in functional arrangements for temporary clamping (102), regularly distributed around the annular flange (30), with m greater than or equal to 1.

19. Container (20) according to claim 18, wherein
the at least one built-in functional locking/unlocking arrangement comprises n built-in functional arrangements for locking/unlocking (112), regularly distributed around the annular flange (30) and the removable cover (28), with n greater than or equal to 1,
wherein the built-in isolation and protection means (124) comprise n built-in functional arrangements for isolation and protection (126), regularly distributed around the annular flange (30) and indexed relative to the n built-in functional arrangements for locking/unlocking (112),
the built-in functional arrangement for temporary clamping (102) and the built-in functional arrangement for isolation and protection (126) are formed by at least one common lug (104, 128), and n is equal to m and the built-in functional arrangements for temporary clamping (102) are indexed relative to the built-in functional arrangements for locking/unlocking (112).

20. Container (20) according to claim 1, wherein the container (20) is disposable.

21. Assembly comprising a chamber (10), a leaktight joining device (40), and a container (20) according to claim 1, for performing the aseptic transfer of a biopharmaceutical product between the chamber (10) and the container (20).

22. Assembly according to claim 21, wherein the chamber (10) comprises a peripheral wall in which is arranged an opening sealed by a removable door, and wherein the leaktight joining device (40) comprises:
stationary temporary clamping means (50) able to keep the container (20) clamped against the chamber (10) so that the removable cover (28) of said container (20) is sealingly held against the removable door (18) of said chamber (10);
stationary unlocking means (60) able to cause the container (20) to transition from an initial locking position where the removable cover (28) seals the container (20) to an intermediate unlocking position where the removable cover (28) is disengaged from the container (20) and is sealingly held against the door of the chamber (10) so as to ensure an aseptic communication between said container (20) and said chamber (10);
stationary locking means (70) able to cause the container (20) to transition from the intermediate unlocking position to a final locking position where said removable cover (28) once again seals the container (20);
an annular functional ring gear (42) able to rotate about a geometric axis of rotation (R) so as to actuate the stationary unlocking means (60) and the stationary locking means (70) of the container (20);
the stationary temporary clamping means (50), the stationary unlocking means (60), and the stationary locking means (70) being mechanically linked to the annular functional ring gear (42) so that one-way rotation of said annular functional ring gear (42) about the geometric axis of rotation (R) successively causes the actuation of the stationary temporary clamping means (50) to hold the container (20) in position against the chamber (10), then the actuation of the stationary unlocking means (60) which causes the container (20) to transition to the intermediate unlocking position, then the actuation of the stationary locking means (70) of the container (20) which causes the container (20) to transition to the final locking position, and the actuation of the stationary temporary clamping means (50) of the container (20) which results in the release of the container (20).

23. Method for aseptic transfer, intended for the aseptic transfer of a biopharmaceutical product between a container (20) and a chamber (10) which are part of an assembly according to claim 21, characterized in that it comprises successive steps consisting of:
providing the chamber (10), the leaktight joining device (40), and the container (20);
positioning the container (20) against a peripheral wall (12) of the chamber (10);
generating an axial clamping of the annular flange (30) of the container (20) against the peripheral wall (12) of the chamber (10) by one-way rotation of an annular functional ring gear (42);
generating the transition of the container (20) from the initial locking position to the intermediate unlocking position by one-way rotation of the annular functional ring gear (42), causing the displacement of the pins at the inner (118) and outer (120) radial positions within the through-housing (114) and blind housing (116);
simultaneously opening a removable door (18) of the chamber (10) and the removable cover (28) of the container (20), the removable cover (28) being sealingly attached against the removable door (18);
aseptically transferring one or more biopharmaceutical product(s) between the container (20) and the chamber (10);
simultaneously closing the removable door (18) of the chamber (10) and the removable cover (28) of the container (20), the removable cover (28) being sealingly attached against the removable door (18);
generating the transition of the container (20) from the intermediate unlocking position to the final locking position by one-way rotation of the annular functional ring gear (42) which causes movement of the pins at the inner (118) and outer (120) radial positions within the through-housing (114) and blind housing (116);
generating the axial unclamping of the annular flange (30) of the container (20) relative to the peripheral wall (12) of the chamber (10) by one-way rotation of the annular functional ring gear (42).

* * * * *